(12) United States Patent
Coffin et al.

(10) Patent No.: US 7,119,904 B2
(45) Date of Patent: Oct. 10, 2006

(54) STABILIZED INFRARED SOURCE FOR INFRARED SPECTROMETERS

(75) Inventors: John M. Coffin, Blue Mounds, WI (US); Robert R. Badeau, Stoughton, WI (US); Michael R. Daun, Madison, WI (US)

(73) Assignee: Thermo Electron Scientific Instruments Corporation, Madison, WI (US)

( * ) Notice: Subject to any disclaimer, the term of this patent is extended or adjusted under 35 U.S.C. 154(b) by 333 days.

(21) Appl. No.: 10/755,928

(22) Filed: Jan. 13, 2004

(65) Prior Publication Data

US 2005/0151082 A1    Jul. 14, 2005

(51) Int. Cl.
*G01B 9/02* (2006.01)

(52) U.S. Cl. .............. 356/451; 356/450; 356/319; 250/504 R

(58) Field of Classification Search ........... 372/29.01, 372/29.011, 29.014
See application file for complete search history.

(56) References Cited

U.S. PATENT DOCUMENTS

| | | | | |
|---|---|---|---|---|
| 3,502,896 A | * | 3/1970 | Langkamp | 307/31 |
| 3,517,167 A | * | 6/1970 | Bell | 250/205 |
| 3,694,624 A | * | 9/1972 | Buchta | 392/407 |
| 3,986,778 A | * | 10/1976 | Mathisen et al. | 356/244 |
| 4,093,991 A | * | 6/1978 | Christie et al. | 356/319 |
| 4,412,744 A | * | 11/1983 | Lee et al. | 356/319 |
| 4,449,821 A | * | 5/1984 | Lee | 356/319 |
| 4,643,571 A | * | 2/1987 | Ferber et al. | 356/326 |
| 4,777,341 A | * | 10/1988 | Steen et al. | 219/121.83 |
| 4,799,001 A | | 1/1989 | Burch | |
| 4,847,878 A | | 7/1989 | Badeau | |
| 5,153,675 A | | 10/1992 | Beauchaine | |
| 5,239,359 A | * | 8/1993 | Allington | 356/319 |
| 5,247,185 A | * | 9/1993 | Herrera et al. | 250/504 R |
| 5,291,022 A | * | 3/1994 | Drake et al. | 250/504 R |
| 5,406,090 A | | 4/1995 | Mattson et al. | |
| 5,747,820 A | | 5/1998 | Karlsson et al. | |
| 5,757,488 A | | 5/1998 | Melton et al. | |
| 5,883,712 A | | 3/1999 | Coffin | |
| 5,896,197 A | | 4/1999 | Coffin | |
| 5,907,430 A | * | 5/1999 | Taylor et al. | 359/350 |
| 5,982,486 A | | 11/1999 | Wang | |
| 6,069,905 A | * | 5/2000 | Davis et al. | 372/50.124 |
| 6,667,808 B1 | | 12/2003 | Clermont et al. | |
| 6,741,629 B1 | * | 5/2004 | Garnache et al. | 372/96 |
| 2005/0073690 A1 | * | 4/2005 | Abbink et al. | 356/451 |

OTHER PUBLICATIONS

Barr, Michael, "Closed-Loop Control", Embedded Systems Programming, Aug. 2002, pp. 55-56 (http://www.netrino.com/publications/glossary/pid.html.*

* cited by examiner

*Primary Examiner*—Layla G. Lauchman
*Assistant Examiner*—Denise B Anderson
(74) *Attorney, Agent, or Firm*—Foley & Lardner LLP

(57) ABSTRACT

An infrared spectrometer includes an infrared source system that is stabilized to provide a substantially constant output light intensity. The infrared source system includes a source element adapted to receive electrical power and to emit light at an intensity related to the electrical power received by the source element. A light detector is mounted in position to receive light emitted from the source element and to provide an output signal related to the intensity of the light received by the detector. A feedback control loop receives the signal from the detector and provides electrical power to the source element to maintain the intensity of the light output from the source element at a selected level as detected by the detector.

19 Claims, 4 Drawing Sheets

STABILIZED INFRARED SOURCE FOR INFRARED SPECTROMETERS

FIELD OF THE INVENTION

This invention pertains generally to the field of infrared spectrometers and particularly to infrared sources utilized in Fourier transform infrared spectrometers.

BACKGROUND OF THE INVENTION

Fourier transform infrared (FTIR) spectrometers are utilized in the analysis of chemical compounds. In these instruments, an infrared source provides a beam of infrared radiation having a band of infrared wavelengths which is passed into an interferometer, typically a Michelson interferometer, and is modulated before being passed through or reflected from the sample to be analyzed. The beam is then directed to a detector. The interferometer modulates the radiation received by it to provide an output beam in which many narrow ranges of infrared wavelengths are typically reduced or enhanced in intensity, with the affected range of wavelengths changing periodically over time. The time correlated output signal from the detector is analyzed by Fourier transformation to derive information on the characteristics of the sample. Examples of FTIR spectrometers and interferometers for such spectrometers are shown in U.S. Pat. Nos. 4,799,011, 4,847,878, 5,153,675, 5,883,712, 5,896,197 and 6,667,808.

Typical infrared sources used in infrared spectrometers use a source element formed of a loop of high resistance electrical conductor, such as silicon carbide, that is supplied with electrical power to be resistively heated to a high temperature that is typically in the range of 1,000° to 1,300° C. At these temperatures, the source element radiates a broad range of infrared light as well as visible light. As used herein, visible and infrared radiation will both be referred to as "light." Generally, the intensity of both the infrared and visible light emitted by the source element is proportional (although not necessarily linearly) to the electrical power supplied to the source element. Commonly used source elements include igniters of the type used in furnaces and stoves. Infrared sources for spectrometers typically include an insulated enclosure surrounding the source element with an opening in the enclosure through which the beam of infrared radiation can exit in a desired direction. An example of an infrared source for infrared spectrometers with a fully enclosed source element is shown in U.S. Pat. No. 5,291,022, which is incorporated by reference. More commonly, the source element is exposed to the surrounding atmosphere.

To obtain consistent spectra from a spectrometer, it is desirable that the intensity of the output beam from the infrared source be relatively constant. Maintaining a constant output from the source is important to spectrometer performance because changes in energy output from the source are reflected in the spectra that are produced by the instrument. For example, a decrease in source energy that may occur between the time when a background spectrum is taken and the time when a sample spectrum is taken will produce a sample spectrum that is erroneously low in energy. Changes in source energy also produce a spectral shift in the instrument line shape due to the black body changes that occur with temperature, and this will also distort spectra produced by the spectrometer.

The source element is typically operated in air, and short-term changes in the surrounding air and purge gas flows within the spectrometer housing can cause short duration changes in the source temperature. Long-term changes in the source temperature occur as the source degrades due to chemical reactions which result from the high operating temperature of the source.

Conventional spectrometers have attempted to maintain the energy output of the source constant by supplying the source element with a constant voltage or current. However, over a long period of time, the output of a typical infrared source element for a given voltage or current input will decline, and most source elements have a non-linear relationship between supply current and element temperature so that control of the voltage or current supplied to the source element does not assure a constant light energy output from the source element over time. Furthermore, most infrared sources have finite lifetimes because of surface oxidation and other problems related to the high operating temperatures (1000° to 1300° C.). The infrared sources can thus burn out, sometimes without advance warning, requiring replacement of the source before further measurements can be done using the spectrometer.

SUMMARY OF THE INVENTION

In accordance with the invention, an infrared spectrometer includes an infrared source system that provides a stabilized infrared output beam that is controlled to a desired intensity so that measurements made by the spectrometer at different times will be more precisely repeatable. The infrared source system includes an infrared source element adapted to receive electrical power and to emit light including infrared light at an intensity related to the electrical power received by the source element. A light detector is mounted in position to receive light emitted from the source element and to provide an output signal related to the intensity of the light received by the detector. A feedback control loop receives a signal from the detector and is connected to the source element to provide electrical power to the source element to maintain the intensity of the light output from the source element at a selected level as detected by the detector. In this manner, short-term fluctuations in source output, such as those which would be caused by ambient air movement or purge gas, can be reduced or eliminated, and changes in source output intensity that occur over time as the source degrades can be corrected so that more accurate measurements are obtained from the spectrometer over the entire lifetime of the source.

The invention also allows a longer source lifetime. The source can be operated at a reduced temperature when the spectrometer is in a standby condition, with the temperature of the source being raised to the normal operating temperature when needed for measurements to be taken. By reducing the temperature of the source a relatively small amount from its normal operating temperature during periods of time when the spectrometer is not being used to make measurements, the overall lifetime of the source can be significantly increased. Furthermore, the invention allows the source output to be maintained at a desired light intensity level without regard to the particular characteristics of the individual source being utilized, so that the normal variability in the operating characteristics between sources does not need to be accommodated. Thus, each individual source can be operated at the lowest temperature necessary to provide the desired output light intensity level, rather than being operated to provide sufficient light output from the least efficient source. The increased lifetime obtainable by operating the source in accordance with the invention permits increased use of an enhanced source mode where the source is heated to an above normal temperature to provide a higher light intensity output that may be useful to obtain good data from a weakly responsive sample being examined by the spectrometer.

Further objects, features and advantages of the invention will be apparent from the following detailed description when taken in conjunction with the accompanying drawings.

DETAILED DESCRIPTION OF THE INVENTION

Figure 1:
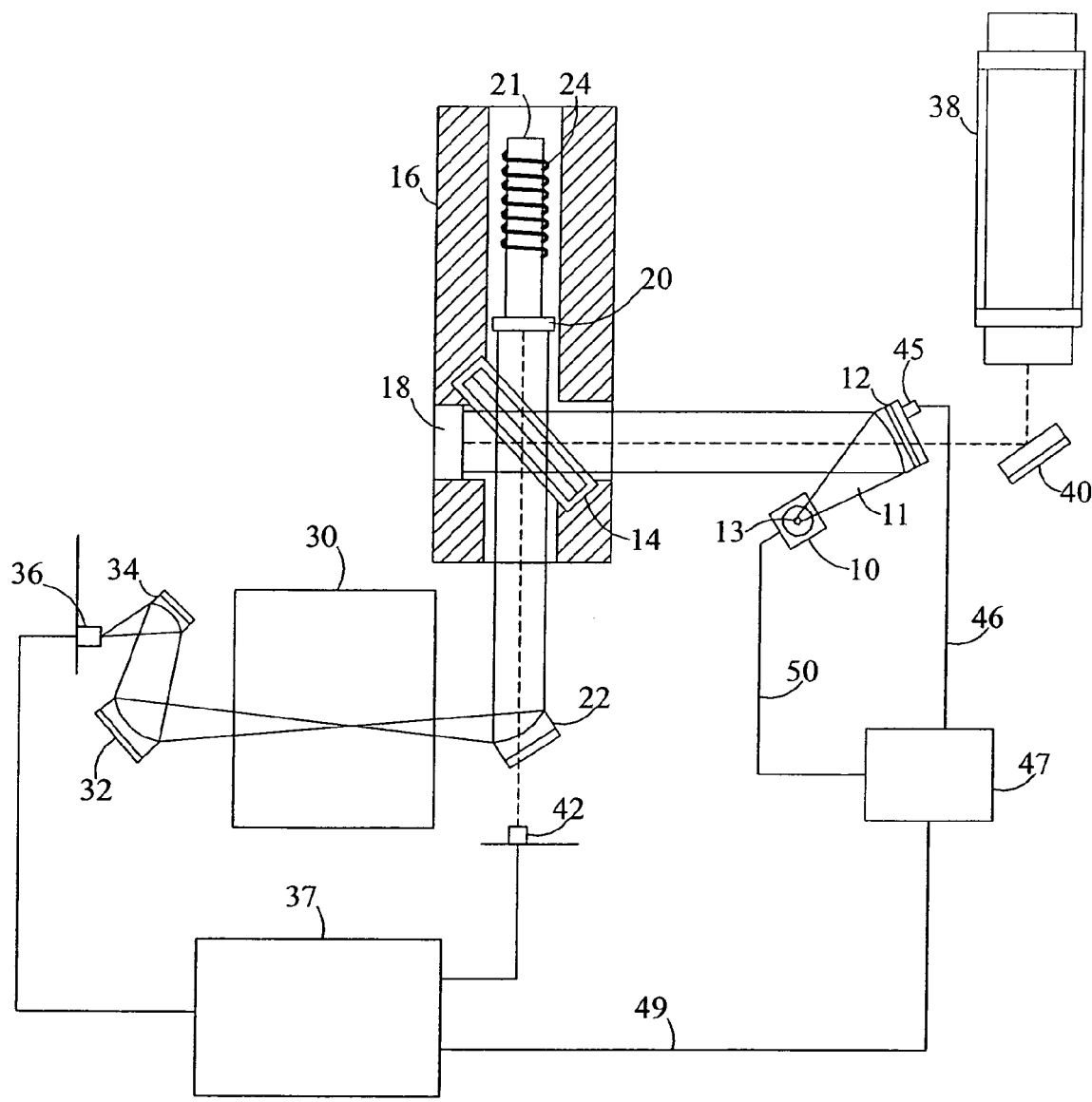
FIG. 1 is a schematic view of the optical elements of an exemplary FTIR spectrometer incorporating the present invention.

For purposes of illustrating the invention, the optical layout of a typical FTIR spectrometer system using a Michelson interferometer is shown in schematic form in FIG. 1. It is understood that such spectrometer systems can be laid out in many different geometries and with various additional features, and the present invention may be utilized in any such various embodiments of spectrometer systems. In the spectrometer system of FIG. 1, an infrared source 10 provides an output beam of light 11 from a source element 13 that is reflected off of a mirror 12, towards a beam splitter 14 within an interferometer housing 16. The light in the beam reflected from the mirror 12 which passes through the beam splitter 14 is then reflected by a reflecting mirror 18 which is located in the optical path of the beam coming from the mirror 12. A light path is formed which is perpendicular to the light path between the mirrors 12 and 18 by recombining light from the first beam with light partially reflected by the beam splitter 14. This path extends between a moving mirror 20 and a focusing mirror 22. The moving mirror 20 moves toward and away from the beam splitter 14. This motion is accomplished by mounting the moving mirror 20 on a shaft 22 which is reciprocated on a linear axis forwardly and rearwardly by voice coil 24. Such interferometers are conventional, and any other interferometer design may be utilized with the present invention.

Light leaving the interferometer housing 16 is reflected by the focusing mirror 22 and directed through a sample chamber 30 from which it goes to focusing mirrors 32 and 34 which focuses the beam onto a detector 36. The electrical signal from the detector 36 is analyzed in a central computer controller 37 of the FTIR spectrometer to carry out appropriate Fourier analysis to determine the spectral characteristics of the substance in the sample chamber 30. To obtain accurate frequency domain information to be generated by the spectrometer, the direction of motion, the speed of motion, and the position of the moving mirror 20 must be controlled at all times. For this purpose, a laser interferometer system is conventionally used to precisely indicate the motion and position of the moving mirror 20. For the purpose of illustrating the implementation of such conventional systems, FIG. 1 illustrates a laser 38, the output of which is directed off a reflecting mirror 40 into the light path of the interferometer housing 16. The laser beam, indicated in dashed lines in FIG. 1, is also split by the beam splitter 14, creating a sinusoidally varying interference pattern in the beam directed toward the mirror 22. The mirrors 12 and 22 are both constructed so that the laser light passes by them so that the laser beam is detected by a detector 42 located behind the mirror 22. The time varying output signal from the detector 42 is digitized and is used by the controller 37 to determine the speed and position of the moving mirror and to correlate the data received from the detector 36 with the position of the moving mirror.

Figure 2:
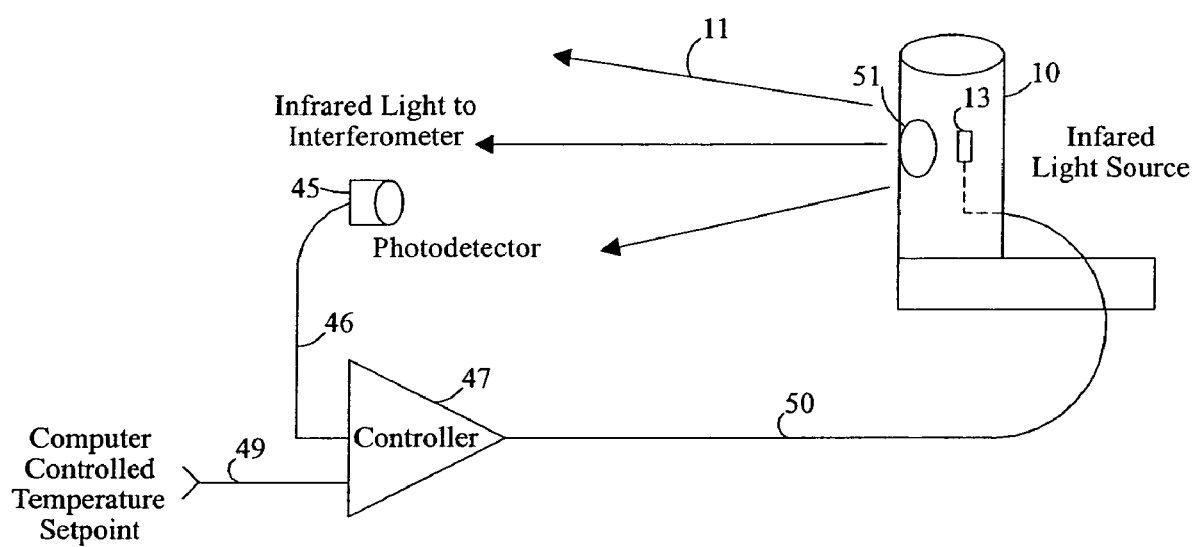
FIG. 2 is an illustrative diagram of a stabilized infrared source system in accordance with the present invention.

In the present invention, a photodetector 45 is mounted to receive the output beam 11 from the infrared source 10, preferably by being mounted at an opening in the mirror 12 so that the detector 45 intercepts a portion of the light in the beam 11 emanating from the source 10. The output signal from the detector 45 on a line 46 is directed to a source controller 47. As illustrated in FIGS. 1 and 2, the controller 47 receives a signal on a line 46 from the detector 45 and provides output power on a line 50 to the source 10 that is controlled to maintain the light output from the source 10 in the beam 11 at a desired intensity level. The source 10 may include an insulated housing as shown in FIG. 2 that surrounds the source element 13 except at a window or opening 51 from which the light beam 11 exits the source.

Figure 3:
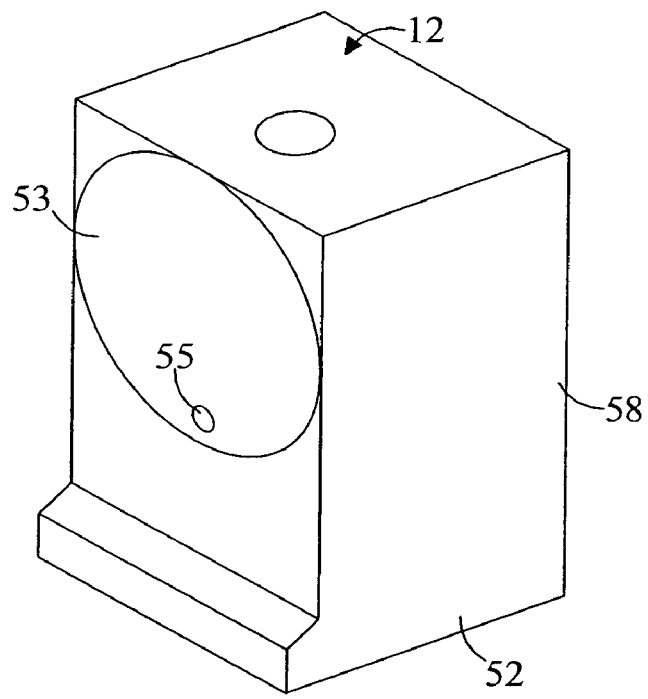
FIG. 3 is a perspective view of a mirror of the spectrometer of FIG. 1 which can be used for mounting the detector of the stabilized source of the invention.
Figure 4:
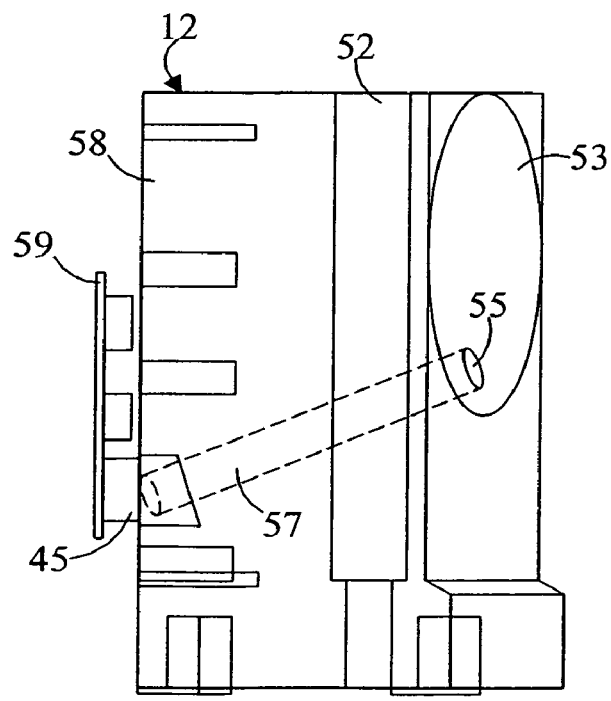
FIG. 4 is a side view of the mirror of FIG. 3.

A convenient and preferred location for the detector 45 is a position mounted to the mirror 12 in a manner to receive a narrow field of view of the infrared source. The preferred mirror mounting structure is illustrated in FIGS. 3 and 4. The mirror 12 is formed in a conventional fashion, having a mirror body 52, which may comprise a block of aluminum, with a mirror face 53 machined into one of the surfaces of the block 52, e.g., by diamond turning, to provide a highly polished, typically parabolic face 53 which is well suited to reflecting infrared light. An opening 55 is formed in the mirror face 53, and as illustrated in FIG. 4, opens into a cylindrical hole 57 that extends from the mirror face 53 to the back surface 58 of the mirror block 52. The detector 45 is mounted into the hole 57 at the back surface 58 of the mirror block so as to receive light that passes into the cylindrical bore of the hole 57. The hole 57 is formed to be aimed at the glowing source element of the source 10 so that the photodetector 45 has a field of view restricted by the bore of the hole 57 such that the detector substantially only receives light from the source element 13. For convenience, the detector 45 is preferably mounted to a small circuit board 59 on which are mounted preamplifiers and other signal conditioning circuits that amplify and condition the output signal from the photodetector 45. An example of a suitable detector 45 is the BPW-34 silicon PIN type photodiode available from Centronic, Inc. of Newbury Park, Calif. This photodiode has a spectral range of 350 to 1100 nm. Because the intensity of visible light emitted by a typical infrared source changes generally in relation to changes in infrared light intensity, photodetectors may be used which detect light primarily in visible wavelengths.

The source controller 47 is provided with a computer controlled temperature set point, which may be selected by the user using the system controller 37 via communication lines 49, to maintain the output of the infrared source 10 at a desired intensity level. By comparing the output signal from the photodetector 45 on lines 46 with the set point, the source controller 47 provides power on lines 50 to the source element 13 of the infrared source 10 that is controlled to maintain the desired light intensity level as detected by the detector 45. The invention provides stability of the infrared source over time so that measurements made by the instrument at different times will be more precisely repeatable. The stabilized infrared source in accordance with the invention further allows an increase in the source lifetime, and can be implemented under software control to provide advance warning to a user that the source element is near the end of its useful life. The feedback control system for controlling the output of the source as illustrated in FIG. 2 is able to correct small variations in source output that may occur in milliseconds, as in the case of changes in air currents, and over years as the source degrades. Upon replacement of the source, the stabilized source in accordance with the invention automatically adjusts the power level supplied to the newly installed source, so that it operates with the same output intensity as the original source, thereby minimizing the changes in spectra between measurements taken with the old source and with the new source. The source stabilization system of the invention also reduces the need to carefully match the replacement source with the original source, since any differences between them are automatically compensated, and further reduces the need to match sources being installed in new spectrometers, thereby reducing the time and cost of manufacturing.

Figure 5:
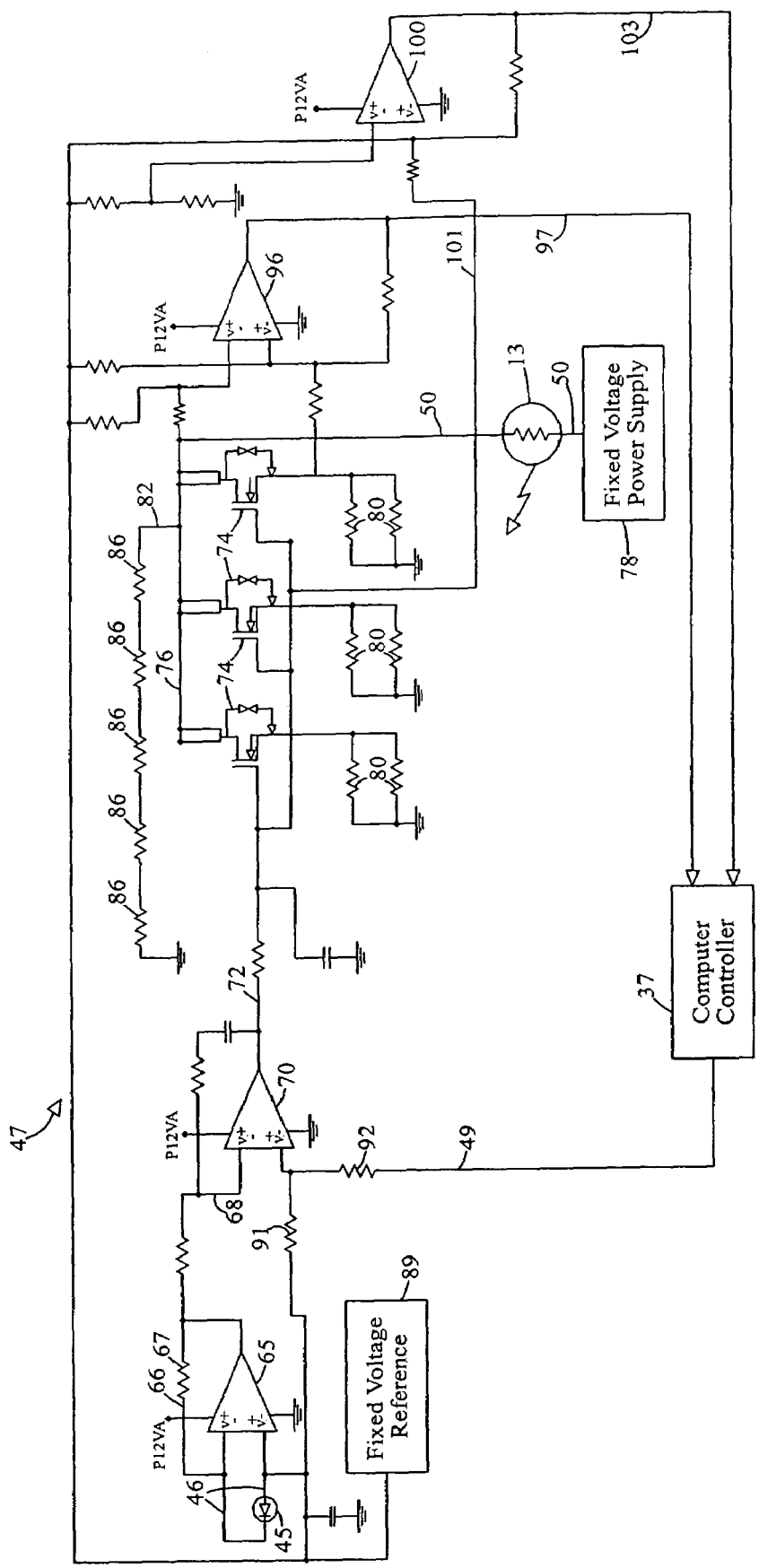
FIG. 5 is a schematic circuit diagram of a feedback control loop for the stabilized infrared source system of the invention.

FIG. 5 is a more detailed schematic circuit diagram of an example of the implementation of the control circuit 47 and the feedback control loop of FIG. 2. It is understood that the circuit embodiment of FIG. 5 is shown for exemplification only, and any other implementation of the control loop may be utilized. For example, although an analog implementation of the control loop is illustrated in FIG. 5, it is readily apparent that the output signal from the photodetector 45 may be digitized and the feedback control carried out in a computer such as a digital signal processor. In the circuit of FIG. 5, the photodetector 45 is connected by the lines 46 to the non-inverting and inverting inputs of a buffer amplifier 65. The amplifier 65 provides an output signal on a line 66 that is proportional to the output signal from the photodetector 45. The signal on the line 66 is provided through a resistor 67 via a line 68 to an inverting input of a differential amplifier 70 which also receives the signal on a line 49 from the computer controller at its non-inverting input. The output of the amplifier 70 on a line 72 is provided to the gates of three parallel connected FETs 74. The FETs 74 are connected between a line 76 and ground, with the line 76 being connected to one of the lines 50 leading to the source element 13. The source element 13 is provided with power from a fixed voltage power supply 78. Thus, when the FETs 74 are turned on by a signal on the line 72, current flows from the power supply 78 through the source element 13 and through the paralleled FETs 74 to ground. The amount of current flow through the FETs 74 will be determined by the magnitude of the signal on the line 72 provided to the gates of the FETs. Resistors 80 may be provided between the FETs 74 and ground to match the current through the different paralleled FETs. If a higher power source is needed, more paralleled FETs can be added as needed. The line 76 is also connected via a line 82 to a set of resistors 86 which are connected between the line 82 and ground. Thus, when the FETs 74 are completely turned off, so that no current flows through them, current will flow from the power supply 78 through the source element 13 and the resistors 86 to ground at a selected minimum level of current flow (determined by the resistance of the set of resistors 86). In accordance with the invention, when the computer controller 37 determines that the spectrometer has not been used to take measurements for a selected period of time, the controller 37 may set a reference signal on the line 49 that turns off the FETs 74 so that the current flowing through the source element 13 drops to a lower level to maintain the source element 13 in a lower temperature standby mode. As shown in FIG. 5, a fixed voltage reference circuit 89 may be provided which provides a fixed voltage on a line 90 through a resistor 91 to the non-inverting input of the amplifier 70, with the signal on the line 49 being provided through a resistor 92 to the non-inverting input of the amplifier 70. In this manner, the voltage at the non-inverting input on the amplifier 70 will be determined by the fixed voltage reference 89 and the signal on the line 49 from the computer controller. As illustrated in FIG. 5, an amplifier 96 may be connected to the line 76 to provide an output signal on a line 97 to the computer controller 37 to provide a computer readable status indicating when the source is below the set point temperature. The below set point signal is created when the voltage across the FETs is less than ½ of a volt, due to the FETs being fully on. Another amplifier 100 may be connected via a line 101 to the gate inputs of the FETs 74 to provide an output signal on a line 103 that provides a computer readable status bit indicating that the source is above the set point temperature. The above set point signal is created when the FETs' gate voltage is below 1 volt which indicates that the FETs are fully off.

The lifetime of an infrared source depends on the source operating temperature. The higher the temperature of the source element, the sooner the source will chemically degrade to the point where it must be replaced. Source degradation tends to increase the electrical resistance of the source over time. As the resistance increases, the current drawn and the resulting heating of the source element decreases, with resulting reduced light output intensity. The present invention allows the average temperature of the source to be reduced, thereby allowing source lifetime to be increased.

As the infrared source ages and its resistance increases, the source light output intensity will decrease and the present invention will automatically increase the voltage of the electrical power supplied to the source to maintain the intensity of the source output at the correct level. Eventually, the source will fail when the source controller reaches the maximum output voltage that it can provide to the source, after which, as the source continues to age, the source intensity will inevitably decrease. The source control system in accordance with the invention can detect this rise in resistance of the source and provide a warning to the user that the source is at the end of its useful life.

The present invention provides correction for changes in purge flow, purge gas (e.g., $N_2$ instead of air), environmental temperature, and changes in the resistance of the connectors and wires supplying power to the source. These variables can cause short-term variation in source temperature and output. The system can respond to small changes in temperature in much less than a second, as well as correcting for long-term changes in the source as it ages in normal operation.

The present invention allows longer source life because all of the sources used in a line of spectrometers operate at a single standard controlled operating temperature, so that there is no longer a need to have an average temperature set high enough to accommodate the fact that different sources have different electrical resistance and therefore different operating temperatures. Furthermore, the present invention can be carried out so as to change the operating temperature, under software control from the system controller via the user interface, to allow the source to be operated at reduced temperature when the spectrometer is in a standby condition, or when the source has a performance surplus that allows operation at a lower source temperature. In such cases, only when full performance is needed is the source supplied with sufficient power to drive it to its standard temperature and standard light output intensity level.

The system allows the temperature and light output intensity of the source to be changed by the system software. This allows the source life to be extended by lowering the source temperature automatically when the FTIR spectrometer is not collecting data. Because the source life is greatly extended by a small decrease in temperature, only a small temperature increase is needed to return to normal operating temperature. The time required to raise the source temperature to operating condition may be less than 5 seconds in most cases, which is fast enough that the FTIR user does normally not notice a warm-up delay. The small drop in source temperature allows the system to be operational with slightly reduced performance at the lowered standby temperature. The system thermal stability will be only slightly affected because the power and heat released by the source and control system only change by about 20% from maximum to minimum. There are some slight effects caused by the fact that the source insulation does not change temperature as quickly as the source element itself. The source insulation takes a few minutes to fully stabilize at a new temperature. Most users will not see effects of the insulation temperature changes because they are small. Limiting the field of view of the spectrometer to only the source element (by using smaller apertures on the infrared beam from the source) can eliminate these insulation effects. Eliminating the source insulation is possible, but will increase source power consumption.

More generally, the spectrometer in accordance with the invention supplies electrical power to the source element to heat the source element to emit light at an intensity related to the electrical power received by the source element. Power is supplied to the source element during a normal operation mode at a selected operational level. The spectrometer determines when the spectrometer has not been used to take measurements for a selected period of time and thereafter reduces the power supplied to the source element to a lower standby level. When a user operates the spectrometer to take measurements, power is then supplied to the source element at the selected operational level.

The present invention also allows the user to select a "turbo mode" wherein the source light output intensity is increased above a normal operational level for a short period of time to improve the ability of the spectrometer to run difficult low throughput samples. This can shorten the source lifetime, but in many cases the extended life given by automatically lowering the source temperature when the spectrometer is not collecting data will still result in longer overall source life. At the command of a user, the spectrometer changes the light output at which the source element is maintained to a higher level for a selected period of time during which measurements are made, and then changes the intensity level of light output at which the source element is maintained to a lower level.

Examples of the temperatures that can be selected include a standby temperature, which is a minimum power input (that need not be regulated) and which gives a lower than normal average source element temperature of about 950° to 1000° C. depending on the source resistance, and multiple (e.g., 20) temperatures that are regulated. Examples of regulated operational temperatures are 1000, 1040, 1070, 1100, 1120, 1140, 1150, 1160, 1170, 1180, 1200, 1210, 1220, 1230, 1240, 1250, 1260, 1270, 1280, 1290, and 1300 degrees C. These temperatures are typically accurate to plus or minus 15 degrees C. given the fact that different sources may be in slightly different positions and the optical detector 45 reads a source at a different position as having a slightly different temperature.

Most sources (depending on resistance) are not capable of reaching the maximum temperature of 1300° C. The highest operation temperature where source life is limited may be set in software in the controller 37, and preferably is about 1250° C. The normal operation temperature may also be set in software and preferably is about 1150° C. A single adjustment potentiometer can be set to give the correct temperature using a standard source. Normally this adjustment will be done once at the factory and is not adjusted for each different source element.

Because the infrared source system of the invention can signal the spectrometer controller software that the source is not reaching the selected temperature, the software in the spectrometer can signal the user that the source has failed to reach the selected temperature. This would normally be an appropriate time for the user to replace the source element. Over time, the source will age and the maximum possible source temperature will decrease. If the source is capable of reaching 100° more than the desired temperature, it is generally expected that the source would be able to last at least a few additional months or years at normal use. If the maximum temperature attainable is only 10 or 20 degrees higher than the desired normal operating temperature, then the source would generally be expected to fail to reach the desired temperature in a few months and a new source should be ordered.

The software in the main computer controller 37 can use a "temperature is low" signal to perform an automatic source life test by ramping up the source temperature in small test steps. This allows the software to record the maximum possible source temperature by recording the temperature at which the source low temperature signal stays on. As an example, with 20 different temperature steps of about 10° C. each, the test may have about 15 temperature steps of about 5 seconds each, allowing the whole test to take place in less than 2 minutes. This test may be repeated at weekly or monthly intervals, and the test results are stored, providing the software with the data needed to track the aging of the source. The software may then alert the user that the source needs replacement before it actually fails, giving the user or service personnel time to schedule maintenance before it is needed.

With source control utilizing discrete steps (e.g., 20 steps) it may be difficult to track small changes in the maximum temperature over time, which limits the ability to accurately measure the last remaining 20% or so of source life. A way to measure the maximum temperature with more resolution is to take advantage of the fact that the source takes more time to heat up the last 10° C. to its maximum temperature. This delay can be measured by stepping the temperature down, waiting (e.g., 15 seconds) then stepping the temperature back up to highest temperature that the source was previously able to reach, reading the "temperature OK" signal, and noting how long it took the "temperature OK" signal to come on. The longer it takes, the closer the maximum temperature is to the lower limit of a 10° step. This lower maximum temperature indicates that the source is closer to failing. By measuring the time to warm up the last 10°, the remaining life can be measured with about 10 times more resolution.

It is understood that the invention is not confined to the particular embodiments set forth herein as illustrative, but embraces all such forms thereof as come within the scope of the following claims.

What is claimed is:

1. An infrared source system for an infrared spectrometer comprising:
   (a) an infrared source element adapted to receive electrical power and to emit light including infrared light at an intensity related to the electrical power received by the source element;
   (b) a light detector mounted in position to receive light emitted from the source element and to provide an output signal related to the intensity of the light received by the detector; and
   (c) a feedback controller receiving the signal from the detector and connected to the source element, wherein the feedback controller receives a temperature set point and provides electrical power to the source element to maintain the intensity of the light output from the source element at a selected level.

2. The infrared source system of claim 1 wherein the feedback controller includes a power amplifier having an output connected to the infrared source element and an input, the output of the power amplifier proportional to a signal level at the power amplifier input, and further including a summing amplifier having an output connected to the input of the power amplifier and one input connected to the detector to receive the signal therefrom and a second input receiving a reference signal, the summing amplifier providing an output signal proportional to the difference between the reference signal and the signal from the detector.

3. The infrared source system of claim 1 wherein the feedback controller comprises software in a computer.

4. The infrared source system of claim 1 wherein the light detector comprises a photodiode.

5. The infrared source system of claim 4 wherein the infrared source element when supplied with electricity is heated to emit both infrared and visible light, and wherein the photodiode is sensitive to visible light.

6. The infrared source system of claim 1 further including a mirror mounted to receive light emitted from the source element and to redirect the light on a beam path, further including an opening formed in the mirror and wherein the detector is mounted to the mirror to receive light from the infrared source that is incident on the mirror through the opening in the mirror.

7. The infrared source system of claim 6 wherein the opening in the mirror opens into a hole having a cylindrical bore and wherein the detector is mounted in the hole such that the detector's field of view is limited by the bore of the hole and wherein the source element is in the field of view of the detector.

8. The infrared source system of claim 1 wherein the infrared source element comprises an electrical resistance element.

9. The infrared source system of claim 1 including heat insulation formed about the source element with an opening in the insulation through which a beam of light passes from the source element.

10. A Fourier transform infrared spectrometer system comprising:
    (a) an infrared source system which provides a beam of infrared light comprising:
        (1) an infrared source element adapted to receive electrical power and to emit light including infrared light at an intensity related to the electrical power received by the source element;
        (2) a light detector mounted in position to receive light emitted from the source element and to provide an output signal related to the intensity of the light received by the light detector; and
        (3) a feedback control loop receiving the signal from the light detector and connected to the source element, wherein the feedback control loop receives a temperature set point and provides power to the source element to maintain the intensity of a light output from the source element at a selected level as detected by the light detector;
    (b) an interferometer which receives the beam from the source system and produces a modulated output beam;
    (c) an infrared detector; and
    (d) optical elements forming a beam path directing the modulated output beam to a sample position and thence to the infrared detector to focus the beam onto the infrared detector.

11. The spectrometer system of claim 10 wherein the feedback control loop includes a power amplifier having an output connected to the infrared source element and an input, the output of the power amplifier proportional to a signal level at the power amplifier input, and further including a summing amplifier having an output connected to the input of the power amplifier and one input connected to the light detector to receive the signal therefrom and a second input receiving a reference signal, the summing amplifier providing an output signal proportional to the difference between the reference signal and the signal from the light detector.

12. The spectrometer system of claim 11 further including means for providing a user selected reference signal to the summing amplifier to allow the intensity of the light emission from the source element to be set at a level selected by the user.

13. The spectrometer system of claim 10 wherein the light detector comprises a photodiode.

14. The spectrometer system of claim 13 wherein the infrared source element when supplied with electricity is heated to emit both infrared and visible light, and wherein the photodiode is sensitive to visible light.

15. The spectrometer system of claim 10 further including a mirror mounted to receive light emitted from the source element and to redirect the light on a beam path, further including an opening formed in the mirror and wherein the light detector is mounted to the mirror to receive light from the infrared source that is incident on the mirror through the opening in the mirror.

16. The spectrometer system of claim 15 wherein the opening in the mirror opens into a hole having a cylindrical bore and wherein the light detector is mounted in the hole such that the light detector's field of view is limited by the bore of the hole and wherein the source element is in the field of view of the light detector.

17. The spectrometer system of claim 10 wherein the infrared source element comprises an electrical resistance element.

18. The spectrometer system of claim 10 including heat insulation formed about the source element with an opening in the insulation through which a beam of light passes from the source element.

19. The spectrometer system of claim 10 further including means for determining when the spectrometer system is not being used by a user and controlling the feedback loop to reduce the power to the infrared source element to a lower standby level until a user commands the spectrometer system to return to an operational mode.

* * * * *